United States Patent
Baba et al.

(10) Patent No.: US 6,958,041 B2
(45) Date of Patent: Oct. 25, 2005

(54) ULTRASONIC IMAGING DEVICE (75) Inventors: Hirotaka Baba, Kashiwa (JP); Ryuichi Shinomura, Higashimatsuyama (JP); Yutaka Sato, Kashiwa (JP); Yuichi Miwa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 192 days.

(21) Appl. No.: 10/221,132
(22) PCT Filed: Mar. 12, 2001
(86) PCT No.: PCT/JP01/01901
§ 371 (c)(1),
(2), (4) Date: Oct. 29, 2002
(87) PCT Pub. No.: WO01/66014
PCT Pub. Date: Sep. 13, 2001

(65) Prior Publication Data
US 2003/0092990 A1 May 15, 2003

(30) Foreign Application Priority Data
Mar. 10, 2000  (JP) .......................................... 2000-66764

(51) Int. Cl.$^7$ ................................................. A61B 8/00
(52) U.S. Cl. ...................................................... 600/443
(58) Field of Search ................................ 600/437–472; 128/916; 73/625, 626; 367/7, 11, 130, 138

(56) References Cited

U.S. PATENT DOCUMENTS 5,617,862 A * 4/1997 Cole et al. .................. 600/459
5,865,751 A * 2/1999 Okuno et al. ............... 600/443

* cited by examiner

Primary Examiner—Ali Imam
(74) Attorney, Agent, or Firm—Antonelli, Terry, Stout & Kraus, LLP (57) ABSTRACT

An ultrasonic imaging arrangement performs tentative scanning of ultrasound to the inside of a living body with delay time corresponding to average sonic velocity, calculates delay time error in a delay time error detecting circuit by using received signals from each channel to which delay control has been performed in a digital delay circuit, compares in a delay time comparing unit the calculated data with a plurality of delay time error data corresponding to various sonic velocities using sound velocity as the parameter stored before hand in a sound velocity-derived delay time error storing unit, selects among those sonic velocities the one matching the delay time error data with a sonic velocity selecting unit, and calculates the sonic velocity within the living body. The calculated sonic velocity is fed back to CPU, and the delay data on the delay applied in the ultrasonic scanning is provided to a delay circuit.

17 Claims, 5 Drawing Sheets

ULTRASONIC IMAGING DEVICE

FIELD OF THE INVENTION

The present invention relates to an ultrasonic imaging apparatus for examining internal structure of a living body and goods, such as an ultrasonic diagnosis apparatus used for medical diagnosis, and a non-destructive examination apparatus used for non-destructive examination of goods. More particularly, it relates to an ultrasonic imaging apparatus that can obtain images of high quality even when the internal structure of a living body and goods are different in their propagation velocity of ultrasonic wave.

BACKGROUND OF THE INVENTION

In a linear scanning type ultrasonic imaging apparatus, ultrasound is received and transmitted by simultaneously driving the elements of an arrayed transducer group forming an aperture, which are selected by a aperture-selecting switch to form the aperture for a plurality of ultrasonic array transducers. Then, by shifting the aperture successively, the inside of the living body or goods is linear-scanned by an ultrasonic beam. Also, in a sector scanning type ultrasonic imaging apparatus, the inside of the living body or goods is scanned by inclining the ultrasonic beam, not shifting the aperture. In both the linear method and the sector method, a focus point is set up in the living body or the goods, and then a driving pulse is provided to each transducer in a delay-controlled manner so that all the ultrasonic waves transmitted from ultrasonic transducer group in the aperture can arrive at the focus point simultaneously.

For performing the delay control, a transmission delay circuit is provided. Output of the driving pulse generated from a transmitting circuit is delayed, said driving pulse is supplied to each transducer in the selected aperture through the transmission delay circuit, and ultrasonic beam is transmitted.

Reflection echoes from the object are received by a plurality of the ultrasonic transducers in the receiving aperture selected, and said reflection echoes are input to a receiving circuit connected to this plurality of ultrasonic transducers through an transmitting/receiving separation circuit. Said echoes are turned into signals having a good amplified dynamic range, and then, said signals are converted into digital signals by a plurality of analog digital converters. These signals are time-converted so that all received echoes arrive at the same time and then added up and output with a phase adjustment unit, which is comprised of a digital delay unit and an adder circuit. This output is used as receiving beam signals. Logarithm compression, filtering and γ correction are performed on this output by a signal processing unit, and the output is displayed after performing conversion of the data, such as coordinate transformation, or interpolation.

Delay data for delaying transmission and reception of signals described above is calculated by dividing the distance from each transducer to the focus point by propagation velocity of ultrasound in the object, thus deriving a time value. But, the structure of the medium to be examined is not uniform. Propagating velocity of ultrasound within a body is varied, depending for instance on whether the person is obese or muscular. Thus, in the present circumstance, delay data is set up in the apparatus by positing the average velocity of ultrasonic waves propagating in the living body.

When the actual sonic velocity is exceedingly different from posited velocity due to individual differences, a clear image cannot be obtained since ideal focusing is not performed.

As an example of method of estimating ultrasonic propagation velocity in living tissue, Japanese Patent Laid-open Publication No. Heisei 6-269447 can be referred. In this method, various coefficients of the medium being studied, including sonic velocity, are hypothesized, a hypothetical model of the transformation of a propagating waveform is calculated with a theoretical formula using those coefficients, by comparing the calculated waveform with measured waveform improved estimates of the above coefficients, including sonic velocity, are obtained.

As an example of an ultrasonic diagnostic apparatus performing optimum focusing by correcting the sonic velocity, Japanese Patent Laid-open Publication No. Heisei 2-274235 can be referred. In the apparatus of said example, an operator sets the sonic velocity of the medium from the console and then modifies the focus. Also, as an example of an ultrasonic diagnostic apparatus that can perform focusing automatically in a region where the focus is not made on a sectional image, Japanese Patent Laid-open Publication No. Heisei 8-317923 and No. Heisei 10-066694 can be referred. In the apparatus of this example, the human body is regarded as a non-uniform medium and the delay time is controlled in accordance with the living body, which is the object to be examined. According to this method, optimum focusing can be automatically obtained.

In the art disclosed in Japanese Patent Laid-open Publication No. Heisei 6-269447, however, the medium composition has to be hypothesized and also the calculation method is complicated. Moreover, the long time it takes to do this calculation and compare it with the actual measured waveform is a drawback. The art disclosed in Japanese Patent Laid-open Publication No. Heisei 2-274235 does not contain a method of automatically estimating sonic velocity, it puts a great burden on the user, as well as lacking accuracy. Moreover, since the arts shown in Japanese Patent Laid-open Publication No. Heisei 8-317923 and No. Heisei 10-066694 do not attempt the estimation of sonic velocity of the medium, good images cannot be obtained for the whole range of ultrasonic beam scanning object, which is a problem to be solved.

DISCLOSURE OF THE INVENTION

The first object of the present invention is to provide an ultrasonic imaging apparatus that can calculate sonic velocity of the medium quickly and control delay time using this delay time.

The second object of the present invention is to provide an ultrasonic imaging apparatus having better operationality, which can automatically perform focusing with the sonic velocity suited to the medium, without an operator having to input this sonic velocity.

The third object of the present invention is to provide an ultrasonic imaging apparatus that can perform focusing uniformly and more sharply throughout the whole region which is subjected to ultrasonic beam scanning; that is, throughout the whole image.

Finally, the fourth object of the present invention is to provide an ultrasonic imaging apparatus that can provide the estimated sonic velocity to the operator in visible form.

To achieve the above objects, the present invention comprises:
  an ultrasonic probe having a plurality of built-in transducers for transmitting ultrasound towards an object to be examined and receiving the echoes from it;
  means for converting each echo signal that is output from a plurality of transducers in said ultrasonic probe into digital signals;

phase adjustment means for adjusting phase of echo signals by applying said predetermined delay time data to each digitized echo signal that is output from said digital signal transforming means;

means for calculating delay time data corresponding to ultrasonic propagation velocity in the object, using the output signals from said beam adjustment means;

means for forming received beam signals by applying the delay time data calculated by said delay time data calculating means to output signals from said phase adjustment means; and means for displaying an image on a displaying means by image-processing the received beam signals formed by said received beam signal forming means.

And, said delay time data calculating means is characterized by comprising:

means for calculating delay time errors of said echo signals output from said beam phase adjustment means by comparison with echo signals from the respective transducers that contributes to reception of said echo signals;

storing means for storing data of delay time errors corresponding respectively to a plurality of ultrasonic propagation velocities; and a sonic velocity selecting unit for selecting the ultrasonic propagation velocity by comparing the output of said calculating means with the delay time data stored in said storing means.

Further, said delay time error data storing means is characterized in that delay time errors corresponding to a plurality of ultrasonic transducer channels are stored as a plurality of delay time distributions, using sonic velocity as a parameter.

Further, said delay time error calculating means is characterized in that delay time errors are calculated by using data in the depth direction of a plurality of output signals of a certain region from said phase adjustment means.

Further, said delay time error calculating means is characterized in that delay time errors are calculated by using data for the whole region in the depth direction of a plurality of output data from said phase adjustment means, as well as that this calculation is performed throughout the predetermined ultrasonic scanning region that is formed by a plurality of the received beams.

Further, said ultrasonic imaging apparatus is characterized in that sonic velocity storing means is provided for storing ultrasonic propagation velocity corresponding to a plurality of delay time distributions that are stored in said delay data storing means, and said sonic velocity selecting unit calculates sonic velocity corresponding to the selected delay time data by comparing with contents stored in said sonic velocity data storing means.

Further, said ultrasonic imaging apparatus is characterized by comprising means for displaying the sonic velocity data on the display screen of said displaying means, said sonic velocity data being calculated at said sonic velocity selecting unit.

Further, said ultrasonic imaging apparatus is characterized by comprising means for setting ultrasound propagation velocity estimated from the physical constitution of the object to be examined, and means for calculating errors of propagation velocity using the ultrasound propagation velocity that is set by said setting means, and the ultrasonic propagation velocity in the object that is calculated from output signals of said phase adjustment means, said received beam signal forming means produces received beam signals by adding propagation velocity errors calculated by said calculating means, and ultrasonic propagation velocity that is set at said setting means to output signals of said phase adjustment means.

Further, said ultrasonic imaging apparatus is characterized by comprising means for converting delay time errors calculated by using data of a plurality of output signals in all region in the depth direction from said phase adjustment means into a sonic velocity data distribution, and then displaying it as a sonic velocity distribution image on the screen of said display means.

And further, said ultrasonic imaging apparatus is characterized in that said sonic velocity distribution image is displayed with hues varying in accordance with a difference of sonic velocity, that sonic velocity distribution image is displayed together with and the ultrasonic cross sectional image simultaneously on the display screen of said display means, and said sonic velocity distribution image superimposed on the ultrasound cross sectional image.

BEST MODE FOR CARRYING OUT OF THE INVENTION

Figure 3:
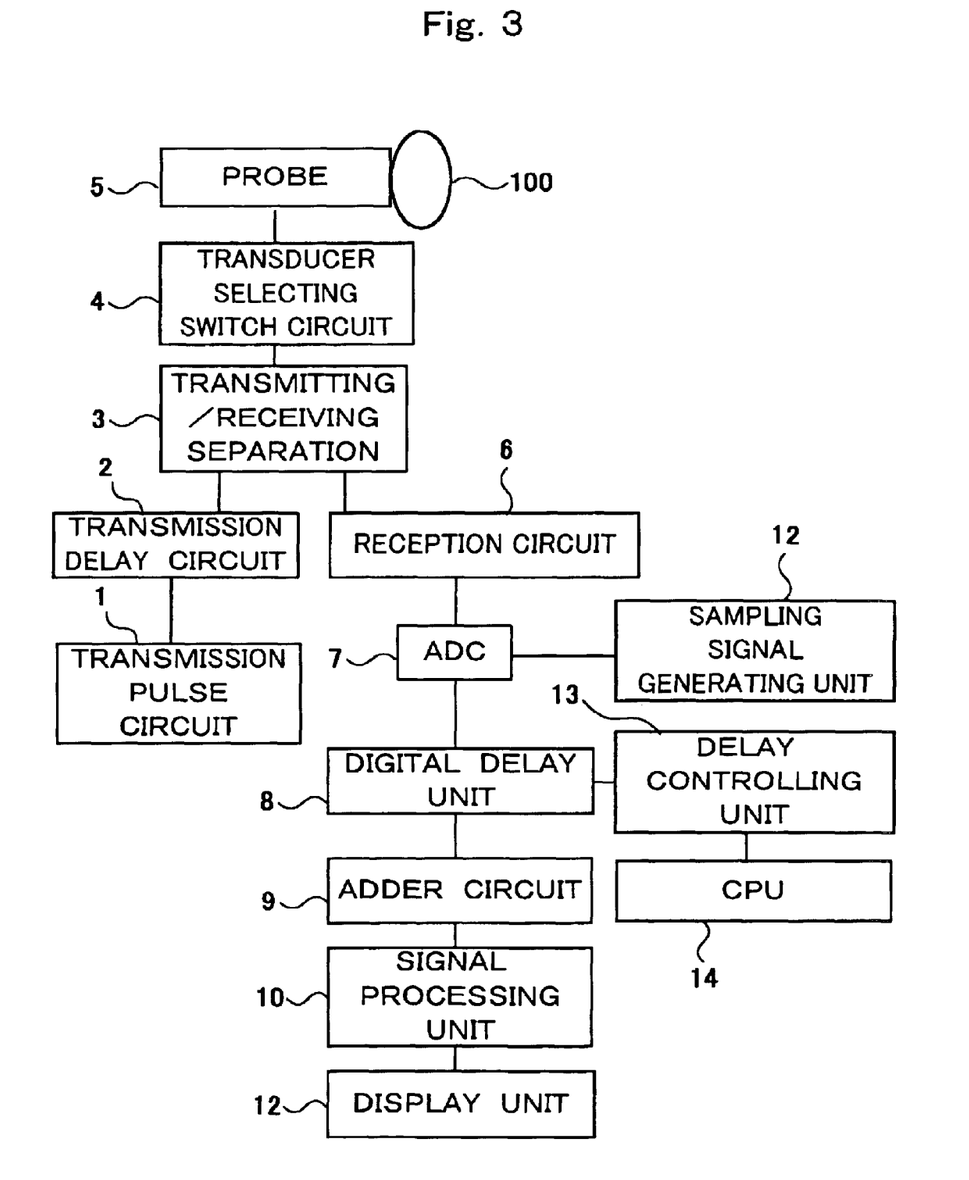
FIG. 3 is a block diagram showing the outline structure of the ultrasonic imaging apparatus of the present invention.

Hereinafter, an embodiment of the present invention is minutely described using diagrams. FIG. 3 is a block diagram showing the structure of an ultrasonic imaging apparatus. In FIG. 3, 1 is a transmission pulse circuit for generating pulse signals for driving ultrasonic transducers to transmit ultrasound. 2 is a transmission delay circuit for providing each ultrasonic transducer driven by the respective pulse signals output from the transmission pulse circuit 1 with the determined delay time corresponding to each driven transducer. 3 is a transmitting/receiving separation circuit for passing signals from the transmission pulse circuit to the ultrasonic transducer when transmitting ultrasonic waves, and from the ultrasonic transducer side to the receiving circuit side when receiving ultrasonic waves. 4 is a transducer selecting switch circuit for selecting from among the ultrasonic transducers that are arrayed on the ultrasonic probe a transducer group (an aperture) to transmit and receive. 5 is a ultrasonic probe having said array of ultrasonic transducers to apply/receive ultrasonic waves to/from a subject or object 100. 5 is a reception circuit for amplifying extremely weak echo signals, which are ultrasonic waves reflected from an object, which then have been converted into an electric signal by the transducer. 7 is an A/D converter (ADC) for converting analog echo signals into a digital signal, said analog echoes being output from the receiving circuit 6. 8 is a digital delay unit for delaying a digital echo signal that is output from the ADC 7. 9 is an adder circuit for forming an ultrasonic receiving beam signal by adding echo signals that are output from the delay unit 8. 10 is a signal processing unit for preprocessing said signals that are output from the adder circuit for conversion to images, that is, performing logarithmic compression, filtering and γ correction on this input signal. 11 is a display unit for successively storing the signals that are output from the signal processing unit 10 together with the position of the respective ultrasonic beam, as well as converting ultrasonic scanning into display scanning to output it, and displaying the image on a displaying device. 12 is a sampling signal generating unit for generating sampling signals at the ADC 7. 13 is a delay controlling unit for providing delay data to the transmission delay circuit 2 and the digital delay unit 8. 14 is a central processing unit (CPU) for collectively controlling said constituent features.

Next, the operation of the ultrasonic imaging apparatus that has the structure shown in FIG. 3 will be described. First, an operator performs initial setting of the apparatus before beginning examination. At the initial setting, the operator identifies the part of the object to be examined, estimates the depth of said part to be examined from the body surface, and sets focusing depth of the transmitting wave. In the apparatus, transmission delay data (Dt) is calculated for this set focusing depth from the determined average value of ultrasonic propagation velocity of the organism by the CPU 14, and then said Dt is provided to the transmission delay circuit 2 through the delay control unit 13 when transmitting. Besides, in order to enable the operator to input sonic velocity manually to the apparatus, sonic velocity inputting device can be furnished in the console and the initial setting can be made with this inputted value of sonic velocity.

At least, after performing said initial setting, the operator applies the ultrasonic probe 5 to the surface of the examined part and inputs a command to begin ultrasonic scanning through the console. Then, the aperture of the probe to be used is selected and the transmission delay data (Dt) is set, and as well the reception delay data (Dr) of digital delay unit 8 at time of reception is set according to said average sonic velocity, and then the scanning begins. When the scanning begins, the driving pulse is output from the transmission circuit 1, and the delay time calculated for each ultrasonic transducer in the above aperture is applied to the driving pulse to be sent to that transducer by the transmission delay circuit 2. Then, the driving pulse is input to the transducer selecting switch circuit (a multiplexer circuit) 4 through the transmitting/receiving separation circuit 3. At the transducer selecting switch circuit 4, connection switchover is performed such that each inputted driving pulse is output to its assigned transducer with the delay time applied to that pulse. The probe is driven with the driving pulse that is output from the transducer selecting switch circuit 4.

The selected transducer group of the probe is driven in order of shortness of delay time of transmission of ultrasound. The ultrasound transmitted from the driven transducer group into the living body propagates within the living body such that every ultrasonic wave surface simultaneously arrives with the same phase at the transmission focus point that is set at the initial setting. Then, when a tissue having different acoustic impedance exists in the propagating course of the ultrasound, a part of ultrasound is reflected at the boundary surface of the tissue and the reflected wave (echo) returns towards the probe. The echoes return to the probe in turn according to the propagation of ultrasound that is transmitted from the shallow part to the deep part of the living body.

Said echoes are received by the transducers driven for transmitting, or by a transducer group of an aperture switched from smaller to larger aperture with the passage of time, and then it is transformed into an electric signal (echo signals). The amplifying process is separately performed at each transducer element line (channel) in the receiving circuit 6 to the echo signals that become electric signals at the transducer, through the transducer selecting switch circuit 4 and the transmitting/receiving separation circuit 3, and then, the amplified signals are inputted to the ADC 7 at the each channel. The ADC 7 converts the echo signals of each channel into digital signals according to the timing of the sampling signals generated by the sampling signal generating means 12. Then, the digitalized echo signals are input to the digital delay unit 8.

The digital delay unit 8 is composed of digital delay circuits for each channel. It performs delay control on inputted echo signals by using said reception delay data that is provided from the delay control unit 13 controlled by the CPU 14, and the echo signals reflected from a certain point in the object (a point along the beam which is received) are outputted to the adder circuit 9 after adjusting the time phase of each channel so that these echo signals are all output at the same time.

The adder circuit 9 adds the echo signals of each channel, which have been outputted from the digital delay unit, forms ultrasonic received beam signals, and outputs them. As a result of said digital delay control and addition, there are formed echo beams that are received by the dynamic focus method well known in this field of the invention. Then, preprocessing such as logarithmic compression, filtering process, or γ correction are performed to the received beam signals, and then the signals are outputted to the display unit 11. The display unit 11 stores inputted beam signals in the memory for a time.

Transmission and reception of said ultrasound and its signal processing are repeated with each selection switchover of the ultrasonic transducer or direction change of ultrasonic beam. The received signals are taken into the display unit in turn, and beam signals inputted by each cycle of said transmission and reception form an image.

And, said stored contents in the memory that have become an image are read out while synchronizing with the scanning of the CRT display. In this manner, the inside of the living body is imaged and displayed.

By using the data obtained by said transmission and reception of ultrasound, the delay control unit 13 calculates the delay data for focusing at the next ultrasonic scanning. The structure and the operation of said delay control unit 13 will be described below.

Figure 1:
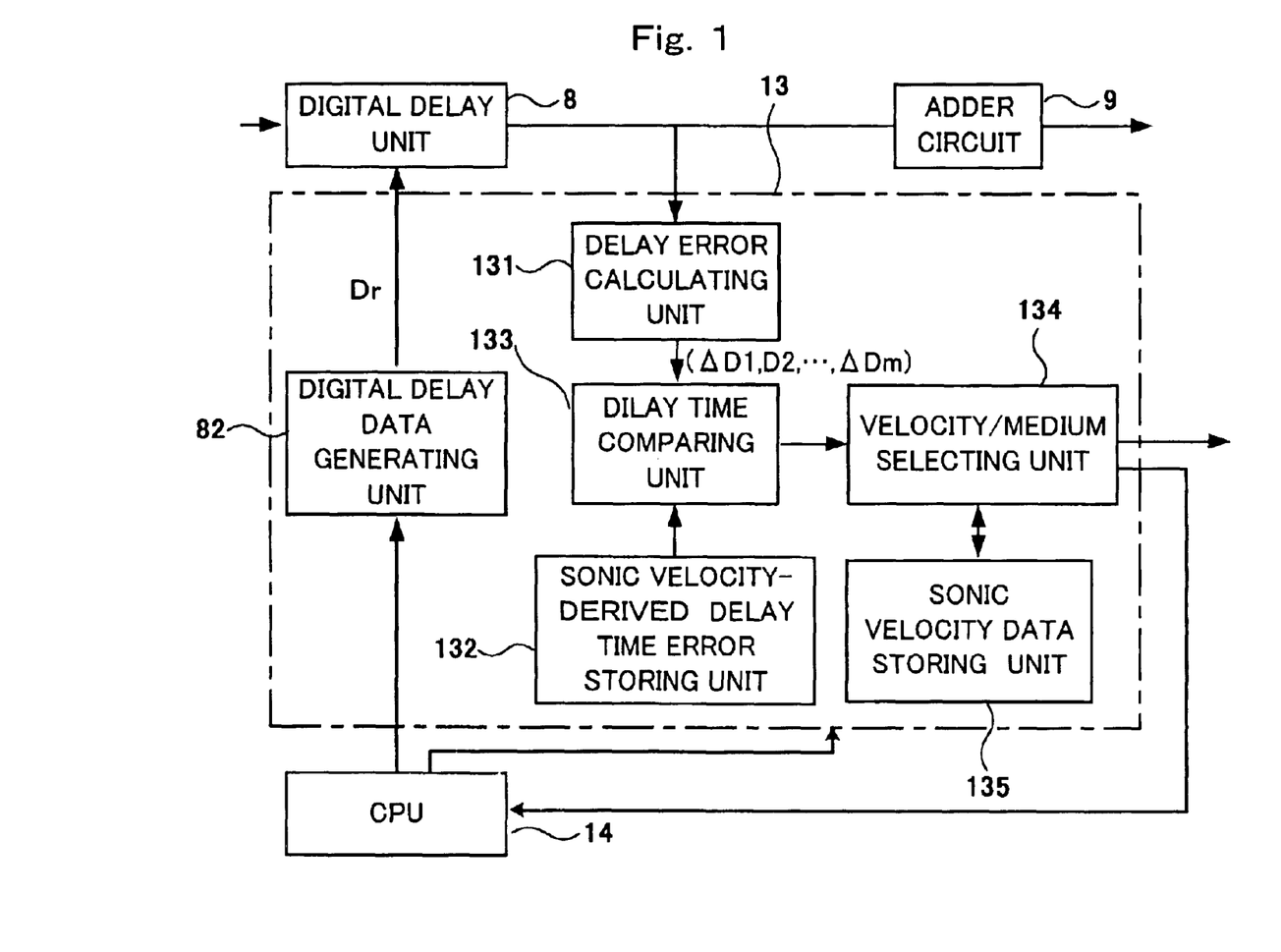
FIG. 1 is a block diagram showing an embodiment of the structure of a delay time controlling unit in an ultrasonic imaging apparatus of the present invention.

FIG. 1 is a block diagram showing the detailed structure of the delay control unit 13 connected to the digital delay unit 8 of the ultrasonic imaging apparatus shown in FIG. 3. In FIG. 1, 82 is a digital delay data generating unit for providing delay data to the digital delay unit 8, and 131 is a delay time error calculating unit to calculate the delay error from a plurality of outputted echo signals, on which delay control has been performed by the digital delay unit 8.

Delay accuracy is improved and a good image can be obtained by adopting the above structure when the calculation result of the delay time error calculating unit 131 is fed back to the digital delay data generating unit 82 to perform delay control for the next ultrasonic transmission and reception. But as for calculation in the delay time error-calculating unit 131, if unexpected signal data is mixed with the data obtained with a tentative scanning, it become difficult to calculate accurate correction value. Therefore, an output of the delay time error calculating unit 131 must be regarded merely as a provisional standard.

Accordingly, an ultrasonic imaging apparatus of the embodiment of the present invention further comprises a sound velocity-derived delay time storing unit 132 that is composed of, for example, ROM for storing in advance a group of delay times corresponding to the sonic velocities of various mediums, the delay time comparing unit 133 for comparing the stored value of delay time error data obtained in the delay time error calculating unit 131 with stored values of the sonic velocity-derived delay time storing unit 132, and outputting the delay time data corresponding to the sonic velocity closest to that of the object, the sonic velocity data storing unit 134 for storing which sonic velocity results in which delay time group stored in the sonic velocity-derived delay time storing unit 132, and the sonic velocity/medium selecting unit 135 for selecting sonic velocity based on delay time data, stored in the delay time storing unit, that had been output by the delay time comparing unit 133.

Figure 2:
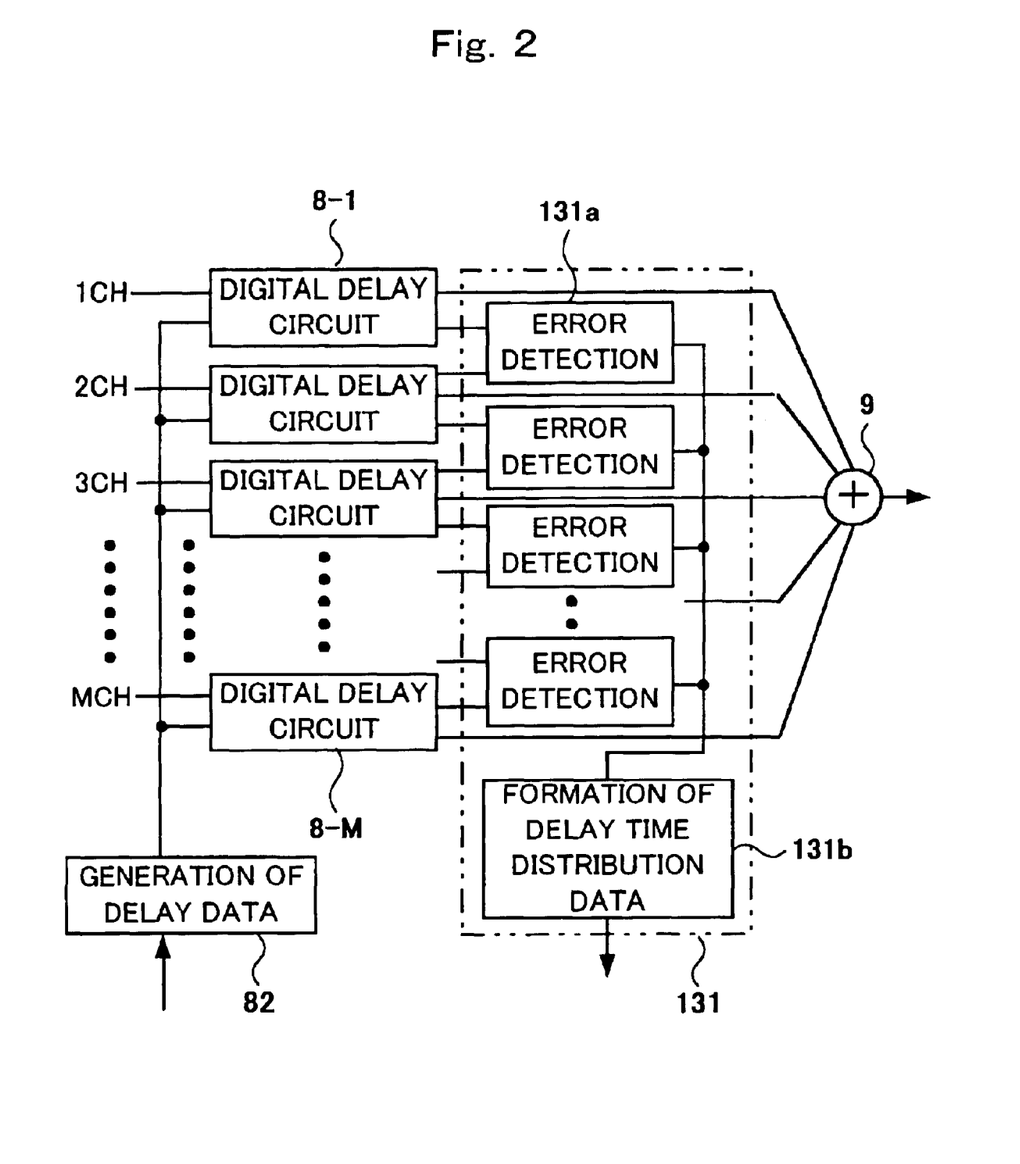
FIG. 2 is a block diagram showing an embodiment of the structure of a delay time error-calculating unit of the present invention.

As is shown in FIG. 2, the delay time error calculating unit comprises delay time error detecting circuits 131*a* of (M−1) in number for detecting delay time errors by inputting the output of the digital delay circuits of two adjoining channels 8-1 to 8-M, and the delay time error distribution data forming circuit 131*b* for expressing output data of this delay time error detecting circuit as distribution data.

Figure 4:
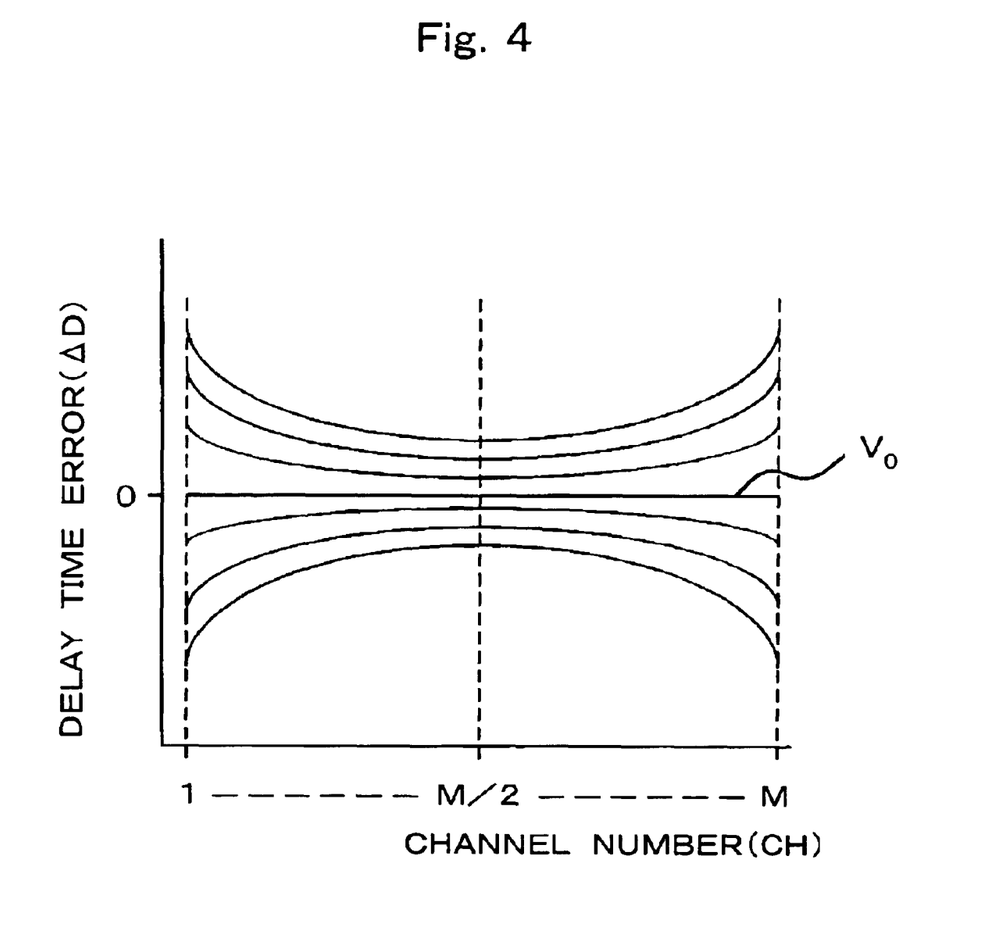
FIG. 4 is a graph representation of contents of the sonic velocity-derived delay time error relations storing unit.

Here, for the sonic velocity-derived delay time storing unit 132, it is preferable to calculate in advance the delay time error data in the case of changing the sonic velocity by predetermined sonic velocity increments or decrements from a certain standard sonic velocity determined, for example, from the delay time error at each channel for said average sonic velocity, and store the data as a table. Then, stored data of this time is made into a graph in order to be visually understood is shown in FIG. 4. In FIG. 4, the horizontal axis indicates the number of the channel and the vertical axis indicates delay time error, and the plurality of lines in the graph indicates the relation between the channels and the delay time error, for a plurality of respective sonic velocities as the parameter. The number of channels of ultrasonic transducers carrying out transmission and reception is M. Incidentally, FIG. 4 is an example of linear scanning. In FIG. 4, sonic velocity Vo is chosen to be that velocity in which the delay time error is the constant value of zero at each channel. This is the reason that the present invention adopts the method of performing a tentative scanning by using the standard sonic velocity Vo, and calculating delay time errors that occur. Referring to FIG. 4, when the sonic velocity is faster than the standard sonic velocity Vo, the delay time error line is convex downward with the lowest point at the center of the group of transducers (M/2). And, when sonic velocity is slower than the standard sonic velocity, the delay time error line is convex upward with the highest point at the center of the group of transducers (M/2). Data stored in the sonic velocity-derived delay time storing unit 132 in this manner, as data for the standard sonic velocity and for velocities deviating from this, contributes to lowering the storage capacity needed in the memory unit.

Thus, by adding the sonic velocity-derived delay time storing unit 132, the delay time comparing unit 133, the sonic velocity storing unit 134 and the sonic velocity/medium selecting unit 135, an ultrasonic imaging apparatus of the embodiment of the present invention enables not only delay time correction for an adaptive imaging method which is generally called, but also estimation of sonic velocity of the ultrasonic propagating medium.

Hereinafter, the principle and the operation of the part of an ultrasonic imaging apparatus containing an embodiment of the present invention concerning the present invention will be described. First, the ultrasonic propagation velocity of the medium is provisionally set to be the average sonic velocity of a living body in the digital delay unit 8 and the transmission delay data based on this average sonic velocity is set in the transmission delay circuit 2, and then ultrasonic scanning of said tentative scanning is performed. The reception delay data (Dr) corresponding to said average sonic velocity is supplied from the digital delay control unit 82 to the digital delay unit 8 so as to receive the echo signals which will be formed into a received beam by the digital delay unit 8, and then the echo signals are input to each channel of the delay time error calculating unit 131. The delay error calculating unit 131 calculates delay time error (Dn) for each channel after the echo signals of adjoining channels such as 1CH and 2CH, 2CH and 3CH, . . . , (M−1)CH and MCH are input in the delay time detecting circuit, using for example the correlation method disclosed in said Japanese Patent Laid-open Publication No. Heisei 4-252576, and then calculates a delay time error data group consisting of D1, D2, . . . , Dm as a distribution data. The purpose of calculating the delay time error data as a distribution is to prevent errors due to said unexpected noise or the like. Incidentally, calculation of the delay time error by the delay error calculating unit 131 can be done for the received beam in all scanning region in case of scanning in the living body while changing the position or the direction of a ultrasonic beam by a probe. It can be also done by setting a region of interest where an organ to be examined exists, and calculating the delay time error of the received beam only in said region.

Next, ultrasonic propagation velocity in the living body is calculated from said distribution of delay time error. In the sonic velocity-derived delay time storing unit 132, delay time data corresponding to plausible sonic velocities is stored in a form making sonic velocity a parameter. Stored contents of said sonic velocity-derived delay time storing unit 132 are also stored as delay time distribution data for each channel in the cases of various sonic velocities. Then, stored contents of the delay error storing unit 131 and the sonic velocity-derived delay time calculating unit 132 are inputted to the delay time comparing unit 133 to be compared, and the delay time distribution in the sonic velocity-derived delay time storing unit 132 which is closest to the distribution of output data from the delay error calculating unit 131 is selected. At this time, the delay time distributions in the sonic velocity-derived delay time storing unit 132, which are the subject with which comparison is made, is stored as delay time distributions for discrete sonic velocity values. Then, if the assumed sonic velocity values are few in number so that there are large gaps, the distribution of output data from the delay error calculating unit 131 does not often match well with the delay time distribution stored in the sonic velocity-derived delay time storing unit 132, and the most closely matching value might be the mean between two of them.

Assuming such a case, it is preferable to add a calculation circuit for selecting two values close to the output from the delay error calculating unit 131 within the delay time error data stored in the sonic velocity-derived delay time storing unit 132, and for performing correction calculation based on an interpolation method or an extrapolation method by using said two values at the latter part of the comparing unit in the delay time comparing unit 133, and use this calculation result for determining sonic velocity. Incidentally, such correction calculation is not necessary when sonic velocity of the medium is estimated to a sufficient degree of accuracy, and this is stored in the sonic velocity-derived delay time storing unit 132. To be able to perform the comparison in the delay time comparing unit 133 simply, it is useful to use a method utilizing the fact that the delay time distribution to the input of a plurality of ultrasound signals can be approximated as a quadratic concave surface to reduce the information to be dealt with. Moreover, calculating the delay time distribution at discrete interval and applying a linear line to the array of delay time discrete value is useful because the information to be dealt with is further reduced.

Next, the stored delay time data for the delay time values matching the output from delay error calculating unit 131 is inputted to the sonic velocity/medium selecting unit 135 and the sonic velocity is calculated referring to the delay time distribution in the sonic velocity storing unit 134.

To improve accuracy of the sonic velocity thus calculated, the received ultrasonic signal must have enough intensity. But in the structure of an apparatus dealing with fundamental waves with the same frequency as the transmitting frequency and harmonic waves generated from an ultrasonic medium, intensity of the harmonic wave is generally weaker than that of the fundamental wave. Thus, it is useful for accurate sonic velocity estimation to make the signal amplification factor of the harmonic wave larger than that of the fundamental wave to compensate for the signal reduction. Similarly, if it is known that the reduction degree of ultrasonic medium is different depending on transmitting frequency and path length, it is effective to amplify the signal by using a correction value that can be calculated in advance.

Figure 5:
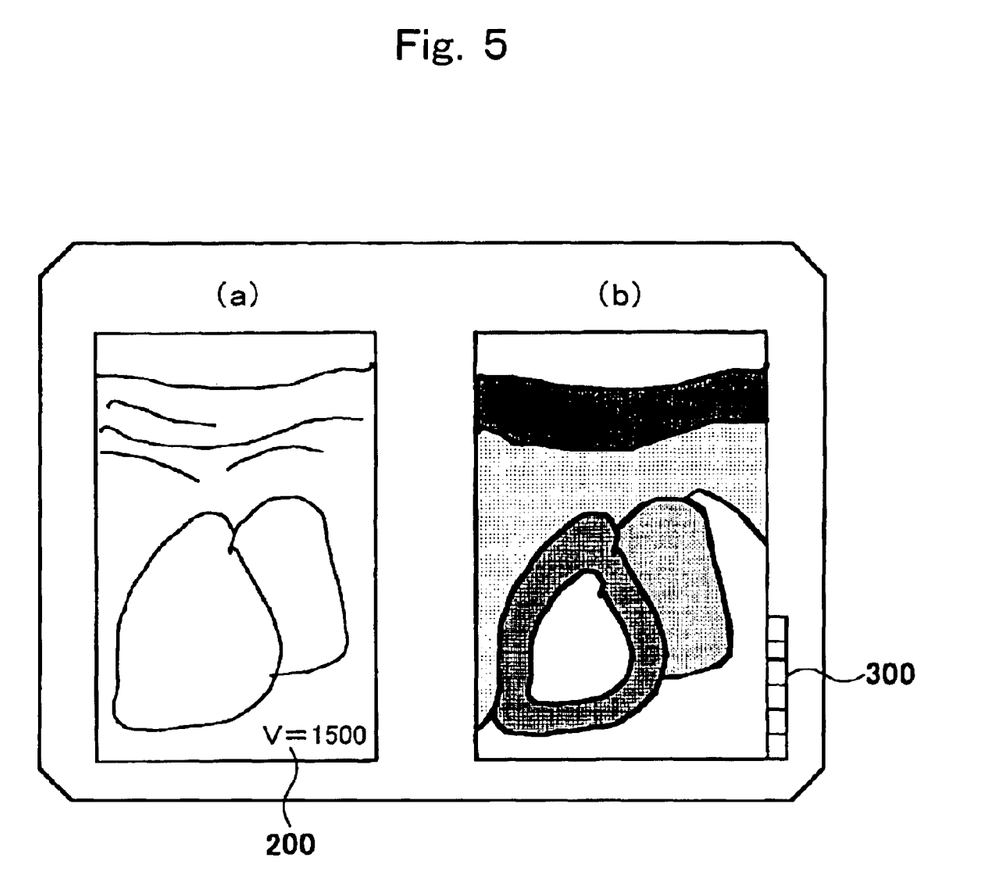
FIG. 5 is a diagram to explain the embodiment of displaying sonic velocity distribution.

The sound velocity data selected by the sonic velocity selecting unit 135 is fed back to the CPU 14 to form the delay data in the digital delay unit 8 for the ultrasonic scanning of the next examination. Also, the sonic velocity data is provided to the display unit 12 through the CPU 14 as a numerical value on the image of the display unit 11, as shown in FIG. 5, where in the area labeled with the number 200 the sonic velocity is shown as V=1,500.

In calculating the delay error at the delay error calculating unit 131, a plurality of delay time error data can be obtained by using the data obtained by scanning the broad region extending both in the depth direction and in the lateral direction. In this method, obtained sound velocities are outputted as different values in a plurality of regions. It is possible to use all these data for scanning in an examination. But there are many cases that it is more useful to use only one sonic velocity representative of the whole region or of the region of interest (ROI). For example, calculating a typical sonic velocity in the whole region and using correction data based on it, an image of average sharpness over the whole region can be obtained. Alternatively, by calculating the sonic velocity only of the ROI and using the correction data based on this only an image in which only the ROI is sharply focused can be obtained. It is possible to use one of these methods selectively or two of them jointly, according to the purpose.

To calculate the sonic velocity that is typical in the whole region, it is useful to add a circuit structure for estimating and selecting from among the sub-regions in this region the sub-region that sends back the most reliable values to the medium/sonic velocity selecting unit 135. For example, if the delay time error distribution outputted from the delay time error calculating unit 131 is tilted, it would appear that the beam would pass through this object in a direction different from the original beam direction, because the beam is made to perform focusing on an object having high level echo. It is difficult to determine the sonic velocity of a region sending back such delay time error values. It also is more difficult to determine sonic velocity as the absolute difference d between the delay time error distribution stored in the sonic velocity-derived delay time storing unit 132 and delay time D' corresponding to said medium becomes larger. Thus it is preferable to select only a region where the intensity A of the received signal is large for calculating the typical sonic velocity.

In other words, an estimated coefficient K for selecting one typical sonic velocity out of sound velocities calculated in a plurality of regions is preferably calculated with the formula $K=A/\alpha+\beta/d+\gamma/\theta$ and then the sonic velocity in the region where K is maximum is selected. Here, $\alpha$, $\beta$, $\gamma$ are values freely chosen for performing suitable weighting to each estimated item.

Also, when calculating the sonic velocity in a specific region, if there is an element moving in the ROI (for example, bodily movement due to heartbeat in a human body) it is effective to continuously transmit ultrasound a number of times to one part and estimate the sonic velocity by averaging the delay error information of each received signal because the sonic velocity is not so affected by the bodily movement and is stable. Further, as for the elements like cardiac valves that move especially fast, it is possible to calculate the sonic velocity accurately by obtaining the delay error information synchronized with the electrocardiogram in addition to the above. And, when the ROI is changed from moving organs to other non-moving organs, it is efficient to switch from the mode of repeated ultrasound transmission at one place to the mode of transmission only one time.

As said delay error measuring calculation methods, there are:

a method of detecting phase difference between adjoining channels by correlation processing;

a method of performing complex multiplication of signals of adjoining channels which have been phased with the main received frequency to isolate the frequency difference component, and then calculating $\tan \theta$ by dividing its real part by the imaginary part to calculate the phase difference; and a method of varying the delay time of each channel so that they converge in order to set the noticed region in displayed to have the maximum histogram height and signal intensity.

Since the delay error calculating unit 131 of the above embodiment is known in said reference, detailed explanation is here omitted. Any of the known methods above can be applied.

The present invention can be modified in various ways. For example, in said embodiment, the sound velocity is calculated and delay data is modified for imaging. But, because the output from the delay error detecting circuit in the latter part of the digital delay unit includes the delay error information, it can be input without modification as the delay error of each channel in the CPU 14, where it is transformed into delay data, input to the delay data unit 82 for imaging, corrected with the average sonic velocity of the whole imaging region to improve the image, and then perform sonic velocity correction only for the ROI according to said embodiment. By this process, the image quality of the whole image can be improved, and the image of the ROI becomes still clearer.

Also, as a method of displaying calculated sonic velocity, the example of displaying the sonic velocity as a numerical value in said embodiment has been explained. However, by scanning ultrasonic beam both in the depth direction and in the lateral direction, the sonic velocity can be calculated in a plurality of regions. If the distribution of all these calculated sonic velocities is made visible in the display, it is possible to observe that the organ is in the process of pathological change even when there is no change of the shape in the living body yet. Various embodiments for displaying it can be considered, display as a sonic velocity map may be the useful method.

Some examples of displaying methods of the sonic velocity map are as follows:

- a method of making a sonic velocity map image such as the one shown in FIG. 5(b) and displaying this and an ultrasonic image (cross sectional image) shown in FIG. 5(a) side by side;
- a method of selecting either the ultrasonic image or the sonic velocity map image for display on a screen of the displaying device;
- a method of displaying the ultrasonic image and the sonic velocity map image overlapped,
- a method of displaying the ultrasonic image by applying to the brightness value of each point on the image a brightness modulation corresponding to the sonic velocity of that point;
- a method of displaying the monochromatic ultrasonic image after adding to each pixel a color modulation corresponding to the pixel of the sonic velocity map image;
- a method of displaying the ultrasonic image superposed on the sonic velocity map where the sonic velocity values are offset from the correspondent pixel of the ultrasonic image.

It is possible to use one of these or a combination depending on the purpose. Of course, it is also useful to display a plurality of the sonic velocities as numerals or to display a typical sonic velocity value selected out of a plurality of sonic velocities by one of the above methods. Incidentally, when displaying the sonic velocity map image, it is helpful to display a scale (300 in FIG. 5) that indicates contrast or color of map image near the map image to help a doctor read it.

Also, when the present invention not only to a B-code monochromatic image used in an ultrasonic image diagnostic apparatus but also a colored image (a color flow mapping image) is applied, it is possible to accurately display the positional relation of the monochromatic image and the colored image. When applied to the monochromatic image and the Doppler image, it is possible to improve accuracy of the positioning of Doppler signal reception region. Further, when applied to an M-mode image, it is possible to improve the distance accuracy. In another method, the degree of improvement of image quality can be indicated by first displaying the image with weak contrast and then displaying the part of the image whose image quality has been improved by lightly displaying it with usual contrast. And when constructing a phase adjustment circuit such that has two lines or shifts among a plurality of lines by time-sharing, the degree of improvement of image quality can be compared because images provided by the usual focus and provided by modified focus can be simultaneously obtained.

And furthermore, complicatedly alternating transmission wave forms are used in the coded transmission and reception, a technique to measure good reflection signals which does not increase the momentary transmission energy but increases the total energy. Thus, it can be inferred that the conventional delay error estimation method described above might easily make a wrong estimate. In this case, after performing usual transmission and reception and improving focusing accuracy by performing said sonic velocity estimation, then, the coded transmission and reception are performed. By this process, the accuracy of the delay time error estimation method can be improved similarly to the usual transmission and reception.

In this embodiment, the case of obtaining two-dimensional sectional images with a one-dimensional array of transducers is described. But also, the same process can be done and the same effect can be obtained in measuring and displaying a two-dimensional or a three-dimensional image by using a ring array or a two-dimensional array of transducers.

As described above, according to the present invention the sonic velocity of the medium can be quickly calculated with a simple calculation without making any assumption about the medium, and ultrasonic imaging can be performed by using the delay time data based on this sonic velocity. Also, the apparatus can automatically calculate suitable sonic velocity without an operator inputting the sonic velocity of the medium. Thus, the operationality of the apparatus is improved.

Furthermore, according to the present invention, a uniform and clearer image can be obtained throughout the whole region of ultrasonic scanning Furthermore, because the apparatus displays the calculated sonic velocity data automatically, the operator can find not only sonic velocity, but also distribution of sonic velocity in the living body.

What is claimed is:

1. An ultrasonic imaging apparatus comprising:
   an ultrasonic probe having a plurality of built-in transducers for transmitting ultrasonic waves towards an object to be examined and receiving the echoes from it;
   means for converting each echo signal that is output from the plurality of transducers in said ultrasonic probe into digital signals;
   phase adjustment means for adjusting phase of echo signals by applying predetermined delay time data to each digitized echo signal that is output from said digital signal converting means;
   means for calculating delay time data corresponding to ultrasonic propagation velocity in the object, using the output signals from said phase adjusting means;
   means for performing delay control for a next ultrasonic transmission and reception by feedbacking the delay time calculated by said delay time data calculating means to said phase adjustment means;
   means for forming received beam signals in response to the delay control; and
   means for displaying an image on a displaying means by image-processing the received beam signals formed by said received beam signal forming means.

2. An ultrasonic imaging apparatus according to claim 1, wherein said delay time data calculating means comprises:
   means for calculating delay time errors from echo signals of a plurality of transducers which are contributed to the signals output from said phase adjustment means;
   storing means for storing delay time error data corresponding to a plurality of ultrasonic propagation velocities; and
   a sonic velocity selecting unit for selecting the ultrasonic propagation velocity by comparing the output of said calculating means with delay time data stored in said storing means.

3. An ultrasonic apparatus according to claim 2, wherein delay time errors corresponding to a plurality of ultrasonic transducer channels are stored as a plurality of delay time distributions using sonic velocity as a parameter, in said delay time error data storing means.

4. An ultrasonic imaging apparatus according to claim 2, wherein said delay time error data calculating means calculates delay time error by using a certain portion of output signals of said phase adjustment means in the depth direction.

5. An ultrasonic imaging apparatus according to claim 2 wherein said delay time error calculating means calculates delay time errors by using output data of said phase adjustment means in all region in the depth direction, as well as that this calculation is performed throughout a predetermined ultrasonic scanning region that is formed by a plurality of received beams.

6. An ultrasonic imaging apparatus according to claim 2, wherein sonic velocity storing means is provided for storing ultrasonic propagation velocity corresponding to a plurality of delay time distributions that are stored in said delay data storing means, and said sonic velocity selecting unit calculates sonic velocity corresponding to the selected delay time data by comparing with the contents stored in said sonic velocity data storing means.

7. An ultrasonic imaging apparatus according to claim 6, said apparatus comprises means for displaying the sonic velocity data being calculated at said sonic velocity selecting unit on the screen of said displaying means.

8. An ultrasonic imaging apparatus according to claim 1, said apparatus comprises means for setting ultrasound propagation velocity estimated from the physical constitution of the object to be examined, and means for calculating errors in this propagation velocity using the ultrasonic propagation velocity being set at said setting means and ultrasonic propagation velocity in the object that is calculated by using the output signal of said phase adjustment means, wherein said received beam signal forming means produces received beam signals by applying propagation velocity errors calculated by said calculating means and ultrasonic propagation velocity being set at said setting means to output signals of said phase adjustment means.

9. An ultrasonic imaging apparatus according to claim 8, said apparatus comprises means for transforming delay time errors calculated by using data of a plurality of output signals of said phase adjusting means on all region in the depth direction into sonic velocity data distribution, and then displaying it as a sonic velocity distribution image on the screen of said display means.

10. An ultrasonic imaging apparatus according to claim 8, wherein the sonic velocity distribution image is displayed with hues varied in accordance with difference of the sound velocity.

11. An ultrasonic imaging apparatus according to claim 8, wherein the sonic velocity distribution image and the ultrasonic cross sectional image are displayed simultaneously on the display screen of said display means.

12. An ultrasonic imaging apparatus according to claim 11, wherein the sonic velocity distribution image is displayed by superimposing the ultrasonic cross sectional image on it.

13. An ultrasonic imaging apparatus according to claim 1, comprising:
    an initial depth input unit to allow operator input of an estimated depth from an object surface of a part of the object to be examined;
    a focusing depth unit to set a focusing depth of transmitted ultrasonic waves taking the operator input of the estimated depth into consideration; and
    a transmission delay data calculating unit to calculate transmission delay data from a determined average value of ultrasonic propagation velocity.

14. An ultrasonic imaging apparatus according to claim 13, comprising:
    a reception delay data set delay of reception delay data from a determined average value of ultrasonic propagation velocity.

15. An ultrasonic imaging apparatus according to claim 13, comprising:
    an average value determining unit to repeatedly transmit ultrasound to the part of the object to be examined a number of times, and to calculate the determined average value of ultrasonic propagation velocity by averaging delay error information of each reception ultrasonic signal.

16. An ultrasonic imaging apparatus according to claim 1, comprising:
    an ultrasound velocity-derived delay time storing unit including non-volatile memory to store in advance a group of delay times corresponding to sonic velocities of predetermined various mediums.

17. An ultrasonic imaging apparatus according to claim 1, comprising:
    an echo signal control unit to output echo signals reflected from a predetermined point in the object after adjusting a time phase for each channel, so that the echo signals are all output at a same time.

* * * * *